United States Patent [19]

Ajemian

[11] Patent Number: 4,624,246
[45] Date of Patent: Nov. 25, 1986

[54] KNEE-SUPPORTING BRACE

[76] Inventor: Krikor Ajemian, 1388 9th Ave., San Francisco, Calif. 94122

[21] Appl. No.: 794,062

[22] Filed: Nov. 1, 1985

[51] Int. Cl.$^4$ ............................................. A61F 3/00
[52] U.S. Cl. .............................. 128/80 C; 128/25 R; 128/78; 128/80 F; 128/165
[58] Field of Search .............. 128/77, 78, 80 C, 80 G, 128/80 F, 80 R, 68, 88, 165, 25 R; 272/130, 126

[56] References Cited

U.S. PATENT DOCUMENTS

| | | | |
|---|---|---|---|
| 1,072,369 | 9/1913 | Spahn | 128/80 F |
| 2,536,454 | 1/1951 | McIntyre | 128/80 G |
| 2,558,986 | 7/1951 | Seelert | 128/80 F |
| 3,976,057 | 8/1976 | Barclay | 272/130 X |
| 4,432,543 | 2/1984 | Normandin | 128/25 R X |
| 4,565,190 | 1/1986 | Pirmantgen et al. | 128/80 C |

*Primary Examiner*—Richard J. Apley
*Assistant Examiner*—Alfedo Acoff
*Attorney, Agent, or Firm*—Flehr, Hohbach, Test, Albritton & Herbert

[57] ABSTRACT

A simply constructed knee-supporting brace comprises a pair of structures to be adapted to be fastened to a leg from both sides of the knee. Each structure includes two elongated solid members rotatably connected to each other which are adapted to be fastened respectively above and below the knee. Two springs connect these elongated members respectively between their upper ends and their lower ends so that the user must exert a force to stretch the springs but the compressed springs aid the user when the knee is straightened as the user stands up.

7 Claims, 3 Drawing Figures

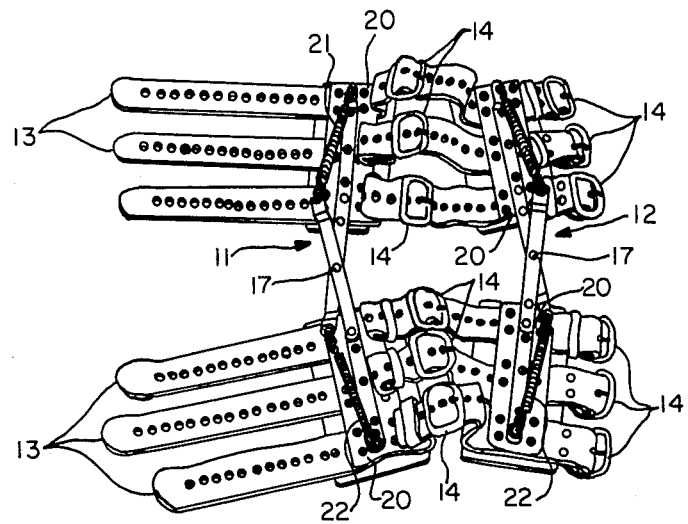
FIG.—1
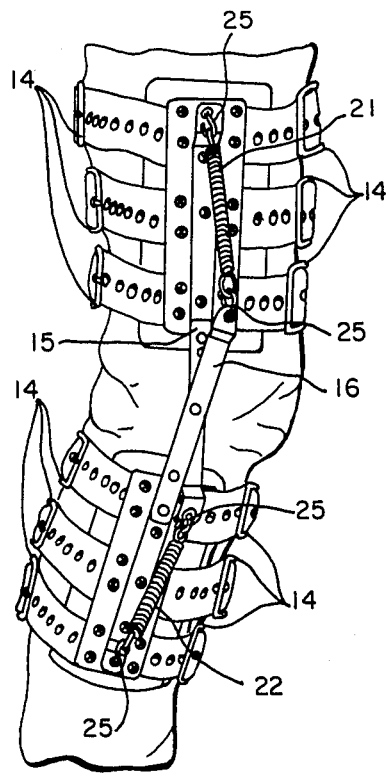
FIG.—2
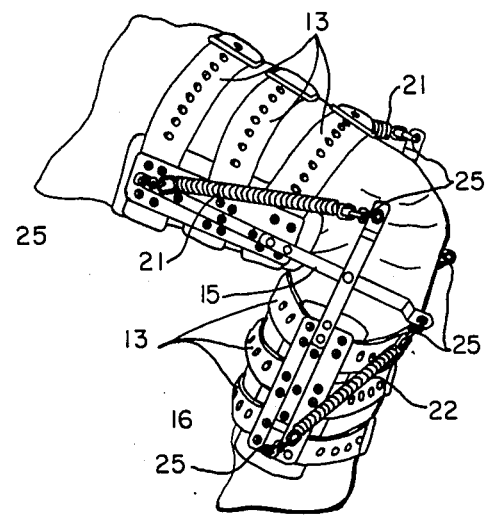
FIG.—3

KNEE-SUPPORTING BRACE

BACKGROUND OF THE INVENTION

This invention relates to a knee-supporting brace and more particularly to a knee-supporting means especially adapted to assist a physically handicapped person with reduced muscle strength in the leg.

Knee-supporting means disclosed in U.S. Pat. Nos. 1,072,369 and 2,267,848 include a stirrup-like member to be securely attached to a leg and are of a relatively complicated structure. A person with weakness in the knee, however, generally has little trouble in bending the knee, for example, to sit down from a standing position because the gravitational force exerted on the upper torso tends to facilitate the lowering of the center of mass of the person. To stand up from a sitting position, by contrast, the person must act against the gravitational force by straightening the knees to stretch the legs. A physically handicapped person frequently finds the need for a supporting means in such situations.

SUMMARY OF THE INVENTION

It is therefore an object of the present invention to provide a knee-supporting brace which is simple in structure.

It is another object of the present invention to provide a knee-supporting brace which is easy to put on and to remove.

The above and other objects of the present invention are attained by providing a knee-supporting brace to be fastened to a leg comprising a pair of structures which are adjustably and removably connected to each other, for example, by straps with buckles. Each of the structures includes two elongated solid members rotatably connected to each other which are adapted to be fastened respectively above and below the knee. Two springs connect these elongated members respectively between their upper ends and between their lower ends so that the user must exert a force to stretch the springs but the compressed springs aid the user when the knee is straightened.

BRIEF DESCRIPTION OF THE DRAWINGS

The accompanying drawings, which are incorporated in and form a part of the specification, illustrate one embodiment of the present invention and, together with the description, serve to explain the principles of the invention. In the drawings:

FIG. 1 is a plan view of a knee-supporting brace embodying the present invention when it is spread out, FIG. 2 is a view of the knee-supporting brace of FIG. 1 when it is worn and the knee is straightened, and FIG. 3 is a view of the knee-supporting brace of FIG. 1 when it is worn and the knee is bent.

DESCRIPTION OF THE PREFERRED EMBODIMENT

As shown in FIGS. 1, 2 and 3 wherein corresponding components are designated by the same numerals, a knee-supporting brace according to the present invention substantially consists of a pair of similarly constructed bendable structures 11 and 12 which are detachably and adjustably connected together by a plurality of strap-like means 13 made preferably of leather. As shown in FIGS. 2 and 3, these two structures 11 and 12 are adapted to be worn by a user on each side of a knee by using buckling means 14 provided on each of the strap-like means 13 to securely fasten the structures 11 and 12 onto the leg. The structures 11 and 12 are constructed similarly, each comprising an upper member 15 and a lower member 16 which are elongated solid steel pieces of about eleven inches (28 cm) in length connected to each other rotatably around a pivot 17. As shown in FIGS. 2 and 3, the upper member 15 is adapted to be worn above the knee and the lower member 16 below the knee. If the two ends of each of the members are called the upper and the lower end with reference to FIG. 2, the pivot 17 is about three inches (8 cm) from the lower end of the upper member 15 and from the upper end of the lower member 16. Flat rectangular plate-like pieces 20 of length of about six inches (15 cm) and width two inches (5 cm) are securely attached to the upper part of the upper member 15 and the lower part of the lower member 16 such that, when the brace is worn as shown in FIGS. 2 and 3, these pieces will be pressed against the user's leg parallel to its surface. The aforementioned strap-like means 13 with the buckling means 14 of a known type are fastened to these pieces 20 by a known method such as by rivet means so that the upper and lower members 15 and 16 of both structures 11 and 12 can be adjustably fastened to the user's leg on both sides of the knee.

Each of the structures 11 and 12 is further provided with two elastic means such as springs. An upper spring 21 connects the upper end of the upper member 15 with the upper end of the lower member 16 and a lower spring 22 connects the lower end of the upper member 15 with the lower end of the lower member 16. The lengths of the springs 21 and 22 are such that they have the unstretched natural length of about 3.5 inches (9 cm) when the user's knee is straight as shown in FIG. 2 with the upper member 15 and the lower member 16 making an angle of about 25°. As the user begins to bend the knee, the angle between the upper and lower members 15 and 16 increases and the springs 21 and 22 are stretched. When the user's knee is fully bent as shown in FIG. 3, the length of the springs 21 and 22 is about nine inches (23 cm).

In summary, the user must exert extra effort while bending the knee because the springs 21 and 22 must be stretched from their unstretched conditions. Generally, however, this does not present any problem even to a physically handicapped user because the bending of the knees usually takes place when the user's center of gravity is being lowered and gravity always makes it easy to lower one's center of gravity. If the seated user wishes to stand up against the force of gravity, by contrast, the restoring forces from the stretched springs tend to aid the user in straightening the knees. In other words, the springs 21 and 22 according to the present invention store energy as the user performs an easier task of bending the knee and come to the aid of the user when a more difficult task of standing up by straightening the knees is performed.

The elastic constant of the springs 21 and 22 should preferably be in the range of two to four pounds/inch (or 360 to 720 gm/cm). It is preferable, however, to have two sets of springs available with different elastic constants so that they can be used interchangeably, depending on the user's choice. For the above and other reasons, it is preferable that the springs 21 and 22 are made easily detachable from the members 15 and 16.

It is further preferable to insert hook-like pieces 25 as shown between the springs and the members. These pieces 25 have the desirable effect of "delaying" the action of the springs. The user generally does not want to feel the effects of the springs all the time. These pieces 25 allow the user to move (bend or stretch) the knee within a certain limit without stretching or compressing the springs. With these hook-like pieces 25 inserted between the springs and the members, the effects of the springs can be felt only if the user bends the knee in excess of a certain minimum angle.

The foregoing description of a preferred embodiment of the invention has been presented for purposes of illustration and description. It is not intended to be exhaustive or to limit the invention to the precise form disclosed, and obviously many modifications and variations are possible in light of the above teaching. For example, the springs 21 and 22 may be replaced by any other elastic means which are now known or to be invented in the future. The buckle straps may likewise be replaced by any similar adjustably fastening means such as adhesive Velcro-type materials. The dimensions of the various components given above by way of example are by no means intended to limit the scope of the invention. Such changes and modifications on the disclosed embodiment that are apparent to a person skilled in the art are intended to be included within the scope of the present invention.

What is claimed is:

1. A knee-supporting brace to be fastened to a leg comprising a pair of structures which are adjustably and removably connected to each other, each of said structures including an elongate upper member having top and bottom ends, an elongate lower member having top and bottom ends and being rotatably connected to said upper member, a first elastic means connected to said upper and lower members at positions near said top ends thereof, and a second elastic means connected to said upper and lower members at positions near said bottom ends thereof, said brace further comprising upper strapping means which are secured to both said upper members of said pair of structures and serve to completely encircle a leg above a knee such that said upper members are adjustably fastened to said leg above said knee, and lower strapping means which are secured to both said lower members of said pair of structures and serve to completely encircle said leg below said knee such that said lower members are adjustably fastened to said leg below said knee.

2. The brace of claim 1 wherein said first and second elastic means are nearly unstretched when said upper and lower members are nearly parallel to each other.

3. The brace of claim 1 wherein said first and second elastic means are springs.

4. The brace of claim 1 wherein each of said structures further includes flat plate-like pieces attached respectively to said upper and lower members.

5. The brace of claim 1 wherein said upper and lower strapping means include a plurality of buckled straps.

6. The brace of claim 1 wherein said elastic means have hook-like pieces through which they are connected to said members.

7. The brace of claim 1 wherein said elastic means are detachably connected to said members.

* * * * *